United States Patent
Lin

(10) Patent No.: US 8,256,663 B2
(45) Date of Patent: Sep. 4, 2012

(54) INSTRUMENT PARAMETER SETTING METHOD

(75) Inventor: Meng-Yi Lin, Taipei (TW)

(73) Assignee: Health & Life Co., Ltd., Taipei (TW)

( * ) Notice: Subject to any disclaimer, the term of this patent is extended or adjusted under 35 U.S.C. 154(b) by 239 days.

(21) Appl. No.: 12/620,055

(22) Filed: Nov. 17, 2009

(65) Prior Publication Data

US 2011/0049231 A1 Mar. 3, 2011

(30) Foreign Application Priority Data

Aug. 31, 2009 (TW) .............................. 98129262 A

(51) Int. Cl.
*G06F 17/00* (2006.01)
(52) U.S. Cl. ...................................... 235/375; 235/380
(58) Field of Classification Search .................. 235/380, 235/375
See application file for complete search history.

(56) References Cited

U.S. PATENT DOCUMENTS

| 6,220,510 | B1* | 4/2001 | Everett et al. ................. | 235/380 |
| 7,325,746 | B2* | 2/2008 | Nishizawa et al. ........... | 235/492 |

* cited by examiner

*Primary Examiner* — Karl D Frech
(74) *Attorney, Agent, or Firm* — WPAT, P.C.; Anthony King

(57) ABSTRACT

An instrument parameter setting device and an instrument parameter setting method are provided. The instrument parameter setting device has a parameter-setting card combined with a biological detection instrument. The parameter-setting card includes a strip area and a first set of block areas. Each block area in the first set of block areas is connected to the strip area respectively. The instrument detects data represented by a logical change of the block areas, so as to set parameters. In addition, it is convenient to input the data into the instrument through an external setting of the instrument. Accordingly, the characteristic parameters of a detection specimen are conveniently input into the instrument, thereby increasing the yield of specimen production, establishing a self-owned technology, and reducing the cost.

14 Claims, 3 Drawing Sheets

INSTRUMENT PARAMETER SETTING METHOD

FIELD OF THE INVENTION

The present invention relates to a parameter setting method and a parameter setting device, and more particularly to a parameter setting method and a parameter setting device for detecting an instrument.

DESCRIPTION OF THE PRIOR ART

A biological sensor is an important instrument for diagnosing and monitoring diseases. Such a sensor is generally used together with a biological sensing specimen for detection. For example, a self-monitoring of blood glucose detector (SMBG) needs to be used together with a blood glucose specimen to detect the blood glucose concentration. The sensing specimen used by such a biological sensor is usually made of disposable materials. When a user purchases each unit of biological sensing specimen, necessary or relevant information of the sensing specimen may need to be input into the biological sensor, such that the instrument can operate correctly and output a correct detection result, or further achieve a system management function. The information may include specimen calibration parameters, sensing function information, specimen expiration-date information, as well as other information that need to be input into the detection instrument. Especially, the specimen calibration parameters are the information that has to be input into the self-monitoring biological detector currently for detection. Due to factors in the manufacturing technology of the biological sensing specimen, each lot of detection specimen has a lot-by-lot characteristic difference. In order to reduce the influence on the detection result caused by the lot-by-lot characteristic difference, an equation is used to represent characteristics of sensing specimens in each lot, and a calibration parameter representing the characteristics of the lot of specimens is given according to the coefficients of the equation. The given characteristic equation is usually a binary linear equation, as shown in Equation 1, in which the slope (a) and the intercept (b) of the characteristic curve are the calibration parameters.

$$y = ax + b \qquad \text{Equation 1.}$$

A manufacturer of the biological sensing specimens must attach the slope and intercept values of the characteristic curve to the lot of detection specimens when outputting the detection specimens, which are referred to calibration codes. When the user starts to use each lot of detection specimens for measurement, the user must perform a setting process according to the user manual, such that the detection instrument is enabled to obtain correct calibration information, so as to obtain correct measurement results.

Currently, two conventional calibration-value setting procedures are provided. In one setting procedure, the user selects a corresponding set of calibration codes built-in an instrument memory according to the calibration codes marked on the package of the lot of specimens. In the other setting procedure, the manufacturer attaches a calibration code card when each lot of detection specimens is delivered. The card uses a memory (usually, an electrically erasable programmable read-only memory (EEPROM)) to store calibration parameters. Before measurement, the user inserts the calibration code card into the instrument, and then the instrument reads the calibration parameters stored in a memory unit on the card, such that the instrument obtains calibration data corresponding to the lot of specimens.

In the first procedure, the calibration parameters need to be predetermined and recorded in the memory of the detection instrument. The number of sets of calibration data is limited by a capacity of the memory, and the characteristics of each lot of detection specimens subsequently produced must be one of the sets of calibration parameters built-in the instrument, which directly influences the production yield of the sensing specimens. Furthermore, the specimen cannot be further used by the original detection instruments, after the characteristics of the specimen is improved or modified. In addition, in the setting procedure, the user needs to perform the settings manually, thereby causing inconveniences in use. Furthermore, if it is set incorrectly due to carelessness, the incorrect interpretation of the measurement may occur.

In the setting procedure using the calibration code card, as the corresponding calibration parameters are stored in an attached calibration code card before each lot of detection specimens is delivered, the problems in the first setting procedure are avoided. In this procedure, the calibration parameters are recorded in the attached calibration code card of each lot of specimens, which are not limited by a memory capacity of the instrument and cause no restrictions to the characteristics of the subsequently produced specimens. However, in such a procedure, a calibration code card needs to be attached to each lot of specimens, and the card at least includes a memory unit, so that the cost is greatly increased.

Both the above procedures cannot realize the objectives of enabling characteristic changes of detection specimens, increasing the yield of specimen production, realizing fast setting, having a low cost, and increasing the setting convenience at the same time. Therefore, a parameter setting method and a parameter setting device capable of achieving all the above objectives need to be provided.

SUMMARY OF THE INVENTION

In order to solve the problems in the prior art, the present invention is directed to an instrument parameter setting device and an instrument parameter setting method, in which the instrument parameter setting device has a parameter-setting card combined with a biological detection instrument. The setting card has an identification indicator that can be corresponding to an input port on a biological sensor. The detection instrument detects a specific data meaning represented by a logical change of the identification indicator, so as to achieve the data setting objective. Furthermore, the present invention is implemented through a non-memory element, so as to be distinguished from the existing patents in the prior art. In terms of inputting calibration data, the present invention can realize the possibility of the characteristic changes of detection specimens, increase the yield of specimen production, establish a self-owned technology, and reduce the cost.

The present invention provides a parameter-setting card, which includes a strip area and a first set of block areas. Each block area in the first set of block areas is connected to the strip area respectively.

The present invention further provides a parameter setting method, which includes the following steps: reading a parameter-setting card, identifying a received logical change, and setting parameters according to the logical change. The parameter-setting card includes a strip area and a first set of block areas. Each block area in the first set of block areas is connected to the strip area respectively.

The present invention further provides a parameter setting method, which includes the following steps: reading a parameter-setting card; identifying a received logical change; and setting parameters according to the logical change. The parameter-setting card includes a strip area and a first set of block areas. Each block area in the first set of block areas is connected to the strip area respectively.

The present invention further provides a device, which includes a micro-controller and a connecting port connected to the micro-controller. The connecting port includes at least one high potential pin and at least one low potential pin. The device uses the connecting port to read a logical change of a parameter-setting card to set parameters.

Other features and advantages of the present invention become more comprehensible through the following accompanying drawings, detailed descriptions, and preferred embodiments.

DETAILED DESCRIPTION

It should be noted that, although one specific exemplary embodiment is provided as an example in the whole discussion, other alternative specific embodiments may also include all aspects without departing from the scope of the present invention.

Figure 1:
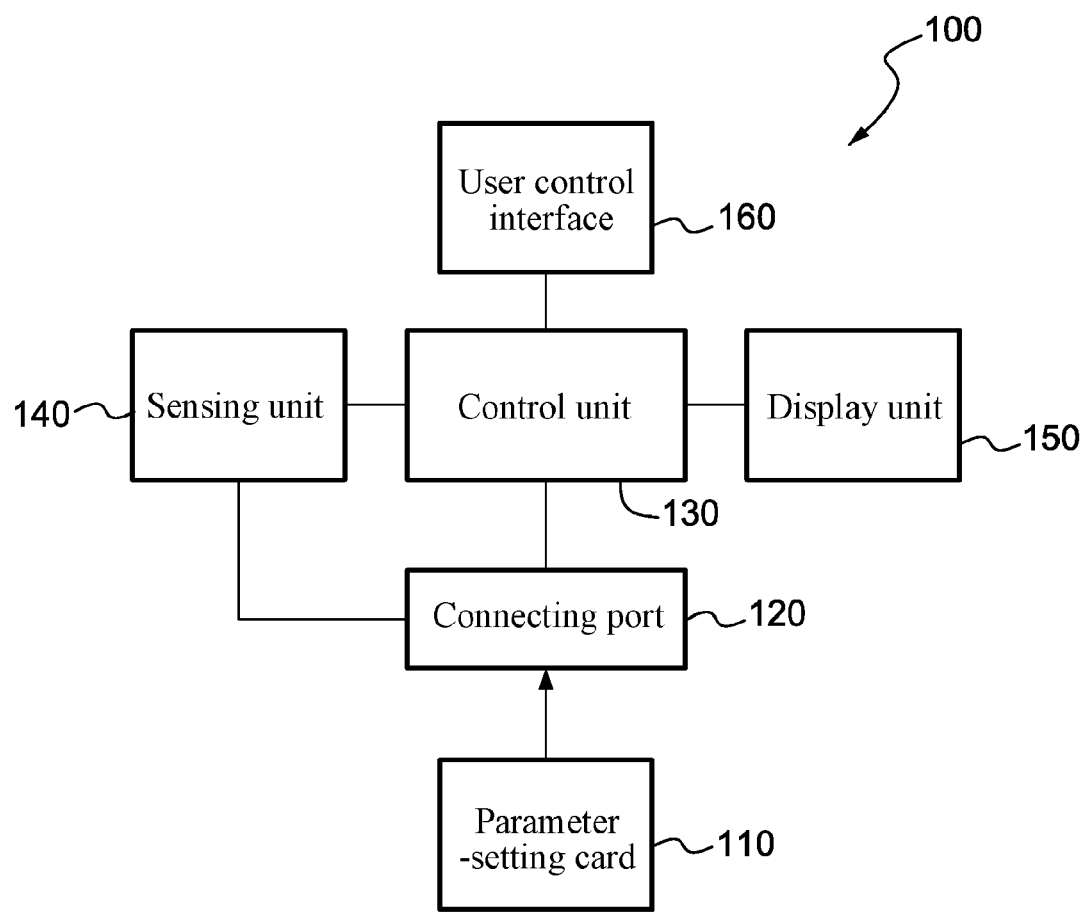
FIG. 1 shows a detection instrument according to an embodiment of the present invention.

FIG. 1 shows a detection instrument according to an embodiment of the present invention. A detection instrument 100 as shown in FIG. 1 includes a parameter-setting card 110, a connecting port 120, a control unit 130, a sensing unit 140, a display unit 150, and a user control interface 160. The detection instrument 100 may be an instrument with a biological detection function, which reads data in the parameter-setting card 110 through the connecting port 120 and the control unit 130 performs parameter calibration according to the read data.

Figures 2, 3:
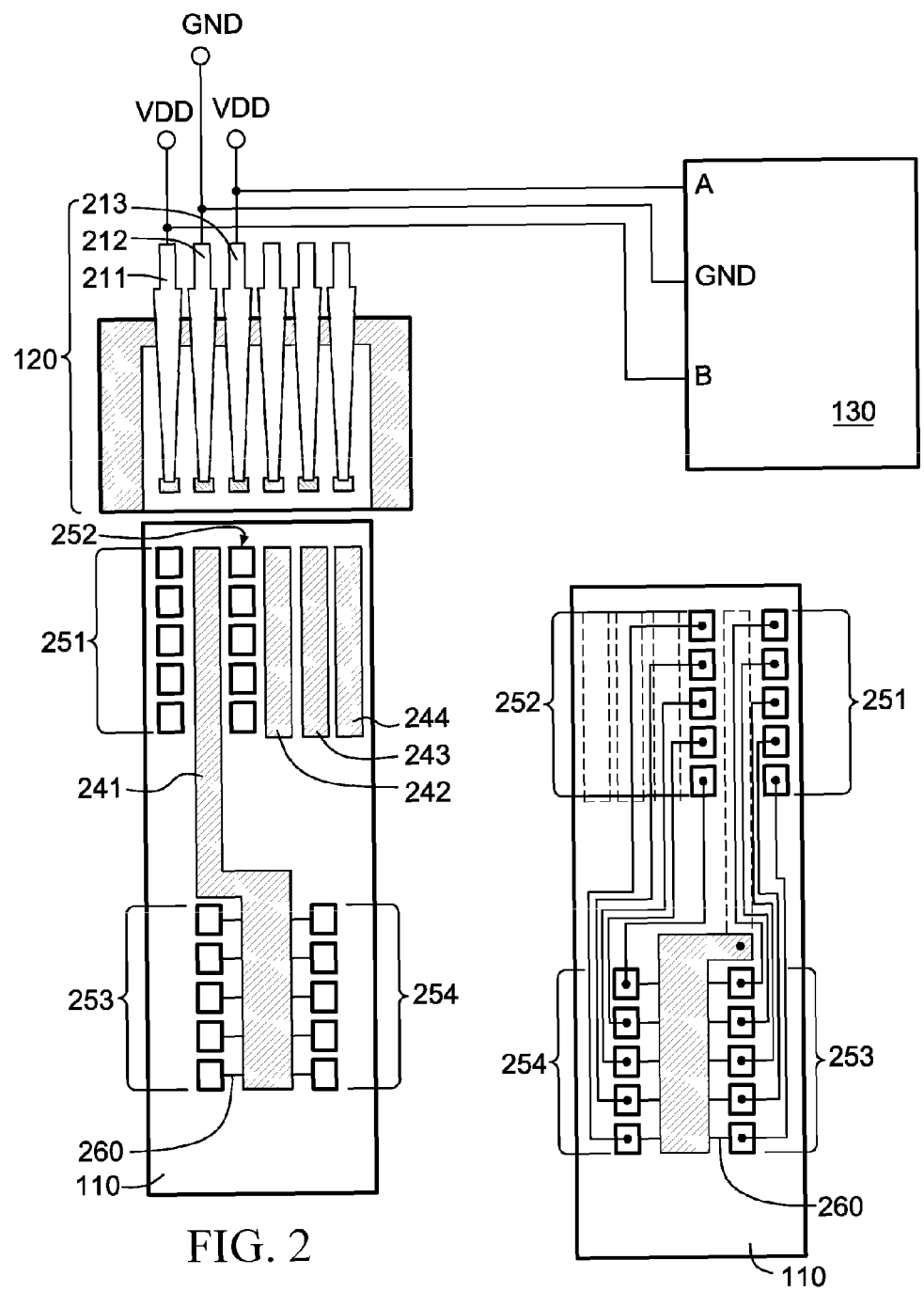
FIG. 2 is a detailed view of a parameter-setting card, a connecting port, and a control unit in FIG. 1.
FIG. 3 is a back view of the parameter-setting card in FIG. 1.

FIG. 2 shows the parameter-setting card 110, the connecting port 120, and the control unit 130 as shown in FIG. 1. Strip areas 241, 242, 243, and 244, first sets of block areas 251 and 252, and second sets of block areas 253 and 254 are disposed on the parameter-setting card 110. Each set of block areas includes a plurality of block areas. In this embodiment, each set of block areas includes 5 block areas. The control unit 130 has two input ports A, B and a ground point GND. A pin 211 is connected to a high potential VDD and the input port B. A pin 212 is connected to the ground point GND. A pin 213 is connected to a high potential VDD and the input port A. The strip areas and the first sets of block areas on the parameter-setting card 110 correspond to each pin of the connecting port 120 respectively. As seen from FIG. 2, the first set of block areas 251 corresponds to the pin 211. The strip area 241 corresponds to the pin 212. The first set of block areas 252 corresponds to the pin 213. The strip area 241 extends to a rear end of the parameter-setting card 110 and is connected to each block area in the second sets of block areas 253 and 254 through a plurality of wires 260 to 269 respectively. FIG. 3 is a back view of the parameter-setting card 110. As seen from FIG. 3, each block area in the first sets of block areas 251 and 252 is connected to each block area in the second sets of block areas 253 and 254 respectively.

Figures 4, 5:
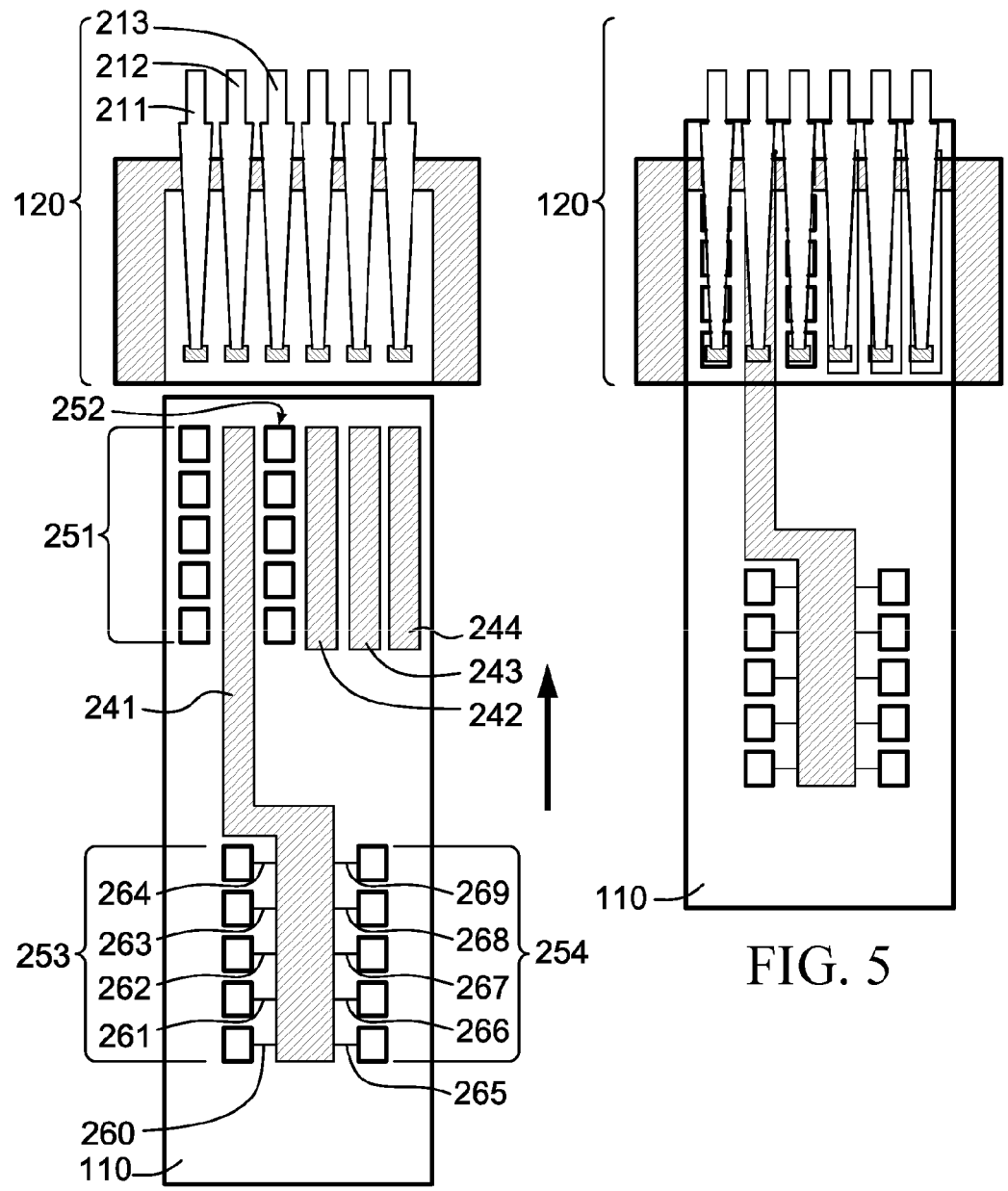
FIGS. 4 and 5 show a process of inserting the parameter-setting card into the connecting port.

FIGS. 4 and 5 show a process of inserting the parameter-setting card 110 into the connecting port 120. Through this inserting motion, each pin of the connecting port 120 can read a logical change, that is, a HIGH/LOW change generated due to the different high or low potential connected to each block area. Each logical change represents a specific data meaning, such that the detection instrument 100 is enabled to perform calibration according to the specific data meaning or perform other functions. The specific data meaning is written in the parameter-setting card 110 in a programming manner and the programming step is very simple, which is different from the method of writing data in the memory in the prior art. For the programming of the parameter-setting card 110, only the wires 260 to 269 between the second sets of block areas 253 and 254 and the strip area 241 need to be cut off, such that the first sets of block areas 251 and 252 represent a specific logical change. For example, if the wires 260 and 262 are cut off, after the parameter-setting card 110 is completely inserted into the connecting port 120, the logical change read by the pin 211 is "LOW, LOW, HIGH, LOW, HIGH", which is turned into a binary code of "00101". In addition, if the wires 266, 267, and 269 are cut off, the pin 212 reads "10110". As known from the above, a default value of each block area is "0" and the block area is set as "1" by cutting off the wire corresponding to the block area. Through this manner, the external data can be programmed in the parameter-setting card 110 and input to the detection instrument 100, so as to achieve effects such as parameter calibration. In order to ensure that the logical statuses read by the instrument are correct, a characteristic that inverted signals are generated when the setting card is inserted and withdrawn may be utilized for making examination. For example, if the logical status is "10110" when the setting card is inserted, the logical status shall be "01101" when the setting card is withdrawn. If the two signals are not inverted signals, it represents that an error occurs in the input process of the setting card, and the user can operate again according to the prompt.

The parameter-setting card 110 in the present invention may also use the same manner to input other external data into the instrument. The programming of the parameter-setting card 110 may be achieved through a PCB engraver, which not only has a low cost, but also processes quickly, thereby avoiding the high cost in the prior art that requires the memory and the inconveniences when the user is required to select calibration codes manually. Such auto-coding can become another calibration system independent from the patent technology about the code card.

The disclosed specific embodiment has been illustrated above to enable any person skilled in the art to manufacture or use the present invention. It is apparent to persons skilled in the art that, various modifications can be made to the specific embodiments, and the general principles defined herein may be applied in other specific embodiments without departing from the spirit or scope of the present invention. Therefore, the present invention is not intended to be limited by the specific embodiment shown herein, and conforms to the widest scope consistent with the principles and novel features disclosed herein. For example, although the number of block areas in each set of block areas on the parameter-setting card in the example is five in the preferred embodiment, it is apparent to persons skilled in the art that the decreasing or increasing of the number of block areas also falls within the scope of the present invention.

LIST OF REFERENCE NUMERALS

100 Detection instrument
110 Parameter-setting card

120 Connecting port
130 Control unit
140 Sensing unit
150 Display unit
160 User control interface
211, 212, 213 Pin
241, 242, 243, 244 Strip area
251, 252, 253, 254 Set of block areas
260, 261, 262, 263, 264 Wire
265, 266, 267, 268, 269 Wire

I claim:

1. A parameter-setting apparatus, comprising:
   a parameter-setting card comprising:
   a strip area; and
   a first set of block areas;
   wherein each block area in the first set of block areas is connected to the strip area respectively through a wire,
   wherein the wire is cut off to program the block area; and
   a device comprising:
   a micro-controller; and
   a connecting port, connected to the micro-controller, and comprising at least one high potential pin and at least one low potential pin;
   wherein the device reads a logical change of a parameter-setting card through the connecting port to set parameters, wherein the logical change is formed by programming the parameter-setting card, wherein the programming the parameter-setting card is accomplished by changing a connection relation between each block area in the first set of block areas and the strip area, and wherein the device reads the parameter-setting card through the connection port and the parameters is set by the logical change during the insertion of the parameter-setting card from an outlet of the connection port to the end of the connection port.

2. The parameter-setting apparatus according to claim 1, wherein the strip area corresponds to a low potential pin of a connecting port and the first set of block areas corresponds to a high potential pin of the connecting port.

3. The parameter-setting apparatus according to claim 1, wherein the strip area corresponds to a high potential pin of a connecting port and the first set of block areas corresponds to a low potential pin of the connecting port.

4. The parameter-setting apparatus according to claim 1, wherein the strip area extends to a rear end of the parameter-setting card.

5. The parameter-setting apparatus according to claim 1, wherein the first set of block areas further comprises a second set of block areas disposed at a rear end of the parameter-setting card, and each block area in the second set of block areas is connected to each block area in the first set of block areas respectively.

6. The parameter-setting apparatus according to claim 5, wherein each block area in the first set of block areas is connected to the strip area through each block area in the second set of block areas, and each block area in the second set of block areas is connected to the strip area through a wire.

7. The parameter-setting apparatus according to claim 6, wherein the wire is cut off to program the block area.

8. The parameter-setting apparatus according to claim 1, wherein the reading the parameter-setting card comprises reading a strip area and a first set of block areas through a plurality of connecting ports.

9. The parameter-setting apparatus according to claim 1, wherein the device further:
   determining whether data is correct or not by reading signals when the parameter-setting card is inserted and withdrawn.

10. A parameter setting method, comprising:
    reading a parameter-setting card by inserting the parameter-setting card from an outlet of a connection port to an end of the connection port;
    identifying a received logical change; and
    setting parameters according to the logical change into a device;
    wherein the parameter-setting card comprises:
    a strip area; and
    a first set of block areas;
    wherein each block area in the first set of block areas is connected to the strip area respectively.

11. The method according to claim 10, wherein the reading the parameter-setting card comprises reading the strip area and the first set of block areas through a plurality of connecting ports.

12. The method according to claim 10, wherein the logical change is formed by programming the parameter-setting card.

13. The method according to claim 12, wherein the programming the parameter-setting card is accomplished by changing a connection relation between each block area in the first set of block areas and the strip area.

14. The method according to claim 10, further comprising:
    determining whether data is correct or not by reading signals when the parameter-setting card is inserted and withdrawn.

* * * * *